United States Patent [19]

Newell et al.

[11] Patent Number: 4,627,432
[45] Date of Patent: Dec. 9, 1986

[54] DEVICES FOR ADMINISTERING MEDICAMENTS TO PATIENTS

[75] Inventors: Robert E. Newell, Pinner; Robert A. Fitzsimmons, Egglestone, both of England

[73] Assignee: Glaxo Group Limited, London, England

[21] Appl. No.: 540,203

[22] Filed: Oct. 7, 1983

[30] Foreign Application Priority Data

Oct. 8, 1982 [GB] United Kingdom ............... 8228887
May 24, 1983 [GB] United Kingdom ............... 8314307

[51] Int. Cl.$^4$ ............................................. A61M 15/00
[52] U.S. Cl. ................................. 128/203.15; 604/58; 128/203.21; 128/200.19; 221/30; 222/88
[58] Field of Search .................. 128/203.15, 200.19, 128/203.21; 604/58, 59, 60; 221/30, 79, 80, 88; 222/88, 83.5, 144.5, 168

[56] References Cited

U.S. PATENT DOCUMENTS

| 3,635,219 | 1/1982 | Altounyaw et al. | 128/203.15 |
| 3,870,046 | 3/1975 | Elliott | 128/203.15 |
| 4,307,734 | 12/1981 | Blankenship | 128/203.15 |
| 4,353,365 | 10/1982 | Hallworth et al. | 128/203.15 |

FOREIGN PATENT DOCUMENTS

| 82/01470 | 5/1982 | PCT Int'l Appl. |  |
| 1526303 | 9/1978 | United Kingdom |  |
| 2061735 | 5/1981 | United Kingdom | 128/203.15 |
| 1603186 | 11/1981 | United Kingdom |  |

Primary Examiner—Henry J. Recla
Attorney, Agent, or Firm—McAulay, Fields, Fisher, Goldstein & Nissen

[57] ABSTRACT

A device for administering medicaments to patients comprises a housing containing a cylindrical chamber. A support is arranged inside the chamber to support a carrier, such as a blister pack. The blister pack has a plurality of containers or blisters arranged in a circle. When a blister pack is located on the support its blisters are located in holes in the support member. A plunger is arranged to enter the chamber through a hole to engage and open a blister registered with it. When the blister is opened, medicament can be withdrawn by a patient inhaling through a mouthpiece. An external member is provided to rotate the support member to register the blister with the plunger in turn. Air can conveniently enter the chamber through a hole in a cover which is removable to permit blister packs to be loaded into the chamber onto the support member.

10 Claims, 5 Drawing Figures

DEVICES FOR ADMINISTERING MEDICAMENTS TO PATIENTS

BACKGROUND OF THE INVENTION

This invention relates to devices by which a medicament can be administered to or by patients inhaling through the devices. The medicaments may be in solid finely divided form or fluid form. Such devices are now quite well known for administering medicaments contained in capsules to patients suffering from bronchial conditions such as, for exammple, bronchial asthma. It is well known for medicament in powder or other finely divided form to be supplied in capsules which are loaded by a patient into such a device which is sometimes called an "insufflator". The medicament is then released from the capsule and inhaled by the patient, usually through the mouth, but sometimes through the nose.

The specification of PCT Application Publication No. WO82/01470 and U.K. Patent Specification No. 1387954 both describe devices for dispensing medicament in finely divided form from capsules. In each of these previously described devices, the capsules are mounted on a rotatable support member on which each capsule in turn can be brought to a position in which it is opened to enable medicament to exit from the capsule to permit it to be inhaled by a patient inhaling through a mouthpiece of the device. In the device described in U.K. Specification No. 1387954, the capsules may be mounted in a so-called blister pack.

There are disadvantages in the use of capsules, which are made of gelatin, to contain medicaments. Gelatin is relatively unstable and is lacking in physical strength so that the capsules need to be protected by packaging, for example in glass bottles. Environmental degradation of both the capsules and their contents may occur in a relatively short time.

An object of the present invention is to provide a more convenient way of administering medicament to such patients than has been possible hitherto and which avoids the need to pack medicaments in capsules. The device of the present invention makes use of the technique of packing medicaments by loading them in blister packs, that is to say, packs comprising a sheet, which may be laminated, of foil or plastics material which acts as a carrier and which is provided with a number of breakable or openable containers called "blisters" incorporating a sheet secured on a first sheet to form a cover or lid. Such blister packs are in common use with tablets of one kind or another, but we have discovered that they can also be used with medicaments in finely divided solid form or in liquid form.

BRIEF SUMMARY OF THE INVENTION

According to the present invention a device for administering medicaments to patients comprises a housing with a cylindrical chamber therein; an air inlet into the chamber; a support inside the chamber arranged to support a carrier provided with a container for medicament or a plurality of containers arranged in a circle; a plunger operable to engage a container registered therewith to open the container in such a way that air being inhaled by a patient will cause the medicament to be released therefrom; means for rotating a carrier on the support to register the container, or each of them in turn, with the plunger; and communicating with the interior of the chamber, an outlet through which a patient can inhale whereby medicament will be released from a container and entrained in the air flow produced by the patient so as to pass through the outlet. The outlet is conveniently but not essentially a mouthpiece by which a patient can inhale.

The device of the invention is suitable for administering a variety of medicaments such as, for example, salbutamol, beclomethasone dipropionate and disodium cromoglycate.

DESCRIPTION OF PREFERRED EMBODIMENTS

Figure 1:
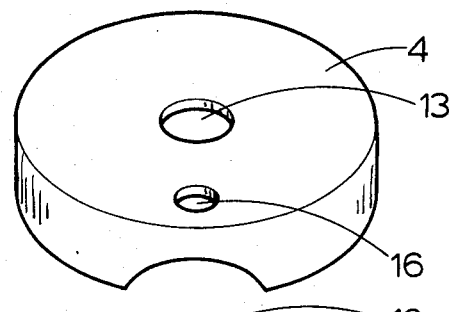
FIG. 1 is an exploded perspective view of a device according to one embodiment of the invention.
Figure 1:
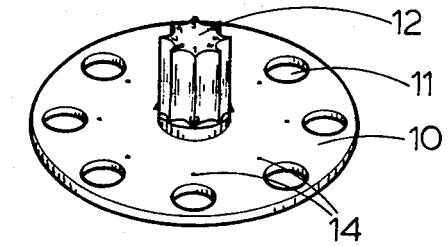
Figure 1:
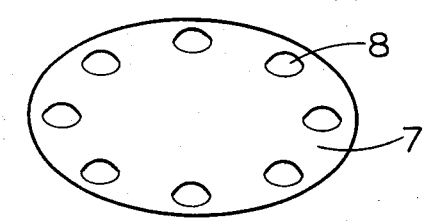
Figure 1:
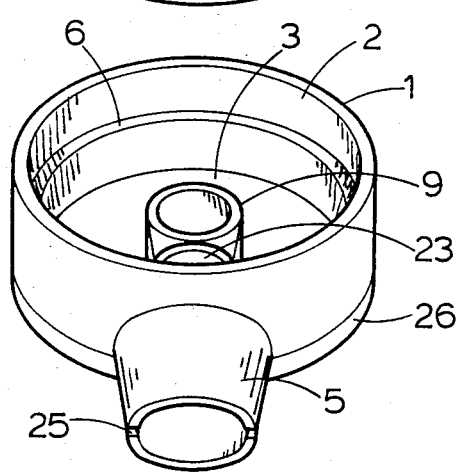
Figure 2:
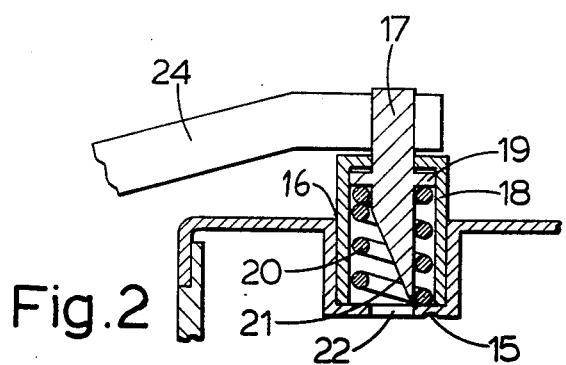
FIG. 2 is a detailed view of a plunger device of the same device.

In the embodiment of the invention illustrated in FIGS. 1 and 2 of the drawings, a medical administration device comprises a shallow cylindrical housing 1 of a plastics material which has a cylindrical chamber 2 therein. The chamber is closed at one end 3, herein considered the bottom of the chamber, and a removable cover 4 is a close fit over the chamber at the other end.

A mouthpiece outlet 5 projects outwardly from the cylindrical wall of the housing 1 and communicates with the interior of the chamber 2. A perforated guard not shown, is provided in the mouthpiece to prevent any solid particles of an undesirably large size being inhaled by a patient inhaling through the mouthpiece.

A rim or shoulder 6 runs round the inside wall of the chamber 2 to provide an annular support on which a blister pack 7 may be located.

The blister pack 7 can conveniently be a foil laminate with a plurality of frangible containers or "blisters" 8 arranged in a circle. The blisters 8 are filled with medicament in particulate form, having a particle size in the range of 0.5-10 microns. The medicament may be with a pharmaceutically acceptable carrier such as lactose or starch in particulate form. Alternatively, the medicament may be in liquid form. The blister pack is of circular disc form, and is removably fitted inside the chamber so that it is replaceable when the individual doses of medicament contained in the blisters have been discharged.

The chamber 2 contains a central open cylindrical support column 9 upstanding from the bottom wall 3 of the chamber. A clamp disc member 10 is removably fitted inside the chamber 2 and has on its underside a plurality of locating pegs, not shown, which pass through the blister pack by an appropriate method and engage inside the support column. The clamp member 10 is rotatable inside the chamber. In use, the clamp member is placed on top of a blister pack 7 which has already been loaded into the chamber and is located on the support shoulder 6. The blister pack 7 is preferably a circular disc of foil laminate material with blisters or containers 8. The clamp member 10 has a plurality of apertures 11 which are arranged in a circle and so spaced from each other that each of them will receive one of the blisters 8 of the blister pack 7. A knob 12 is upstanding from the clamp member 10 and when the lid 4 is fitted on the housing 1 the knob 12 will project through an aperture 13 in the top of the lid 4. This knob can be turned by the patient to rotate the clamp member 10 and since the blisters 8 of the blister pack 7 are located in the apertures 11 in the clamp plate 10 rotation of the clamp member will also rotate the blister pack. A plurality of protuberances or pips 14 are provided on the top of the clamp member 10 and engage in a recess 15, FIG. 2, on the underside of the cover 4 to make sure that the clamp plate is correctly aligned in position. As will be seen, the knob 12 is fluted to provide openings between the knob and the hole 13 through which air can enter the chamber 2 from the outside.

The cover 4 also has an aperture 16 in which a plunger 17 contained in a plunger housing 18 can be received. The plunger has an annular shoulder 19 and a spring 20 can bear between the shoulder 19 and the bottom of the plunger housing 18 to urge the plunger into an upper or inoperative position. The plunger may be provided with a knife edge 21 or other means to enable the blister to be opened. When the plunger 17 is depressed against the action of the spring 20, the lower edge portion 21 of the plunger will pass through an aperture 22 in the plunger housing to pass through a blister 8 located in register with the plunger. Such engagement will open the blister, and permit the release of medicament therefrom. This action will so open the blister that when a patient inhales air will pass through the blister, the medicament being entrained in the air flow and exiting through the mouthpiece 5 via a transfer cavity 23 inside the chamber in communication with the mouthpiece 5. By rotation of the knob 12 the clamp member 10 and the blister pack 7 can be rotated to bring each blister in turn into location beneath the plunger. The various protuberances or pips 14 will in turn engage in the recess 15 to make sure that the blister pack is correctly registered with the plunger.

It is not essential that the plunger have a knife 21 to open the blister. If desired a needle can be used to perforate the blister or the plunger may have a pointed end or even a blunt end or any other convenient opening means may be used.

In use, the patient needing a dose of medicament may hold the device with the mouthpiece in his mouth. The patient then depresses the plunger to open the blister and give access to the medicament therefrom and inhales through the mouthpiece so that the medicament will be entrained in the air flow and will enter the lungs of the patient. If desired, the mouthpiece can be provided with air inlet apertures 25 to improve the air flow as the patient inhales.

In a modification not illustrated the underside of the blister pack can be supported on another clamp plate instead of the support rim or shoulder 6.

The blister pack is conveniently arranged to provide a sufficient number of individual doses for a patient for use during a convenient period such as one day or more. The housing can be modified by providing an additional chamber, not visible, at the bottom, this additional chamber being closed by a removable cover 26. This additional chamber can be used to store replacement blister packs.

The mouthpiece may, if desired, be arranged so that a patient may use it to inhale through the nose.

Figure 3:
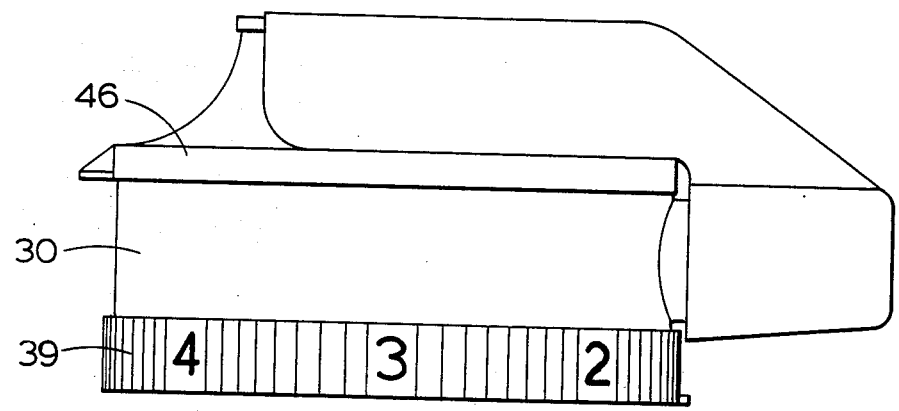
FIG. 3 is an elevation of another embodiment of the invention.
Figure 4:
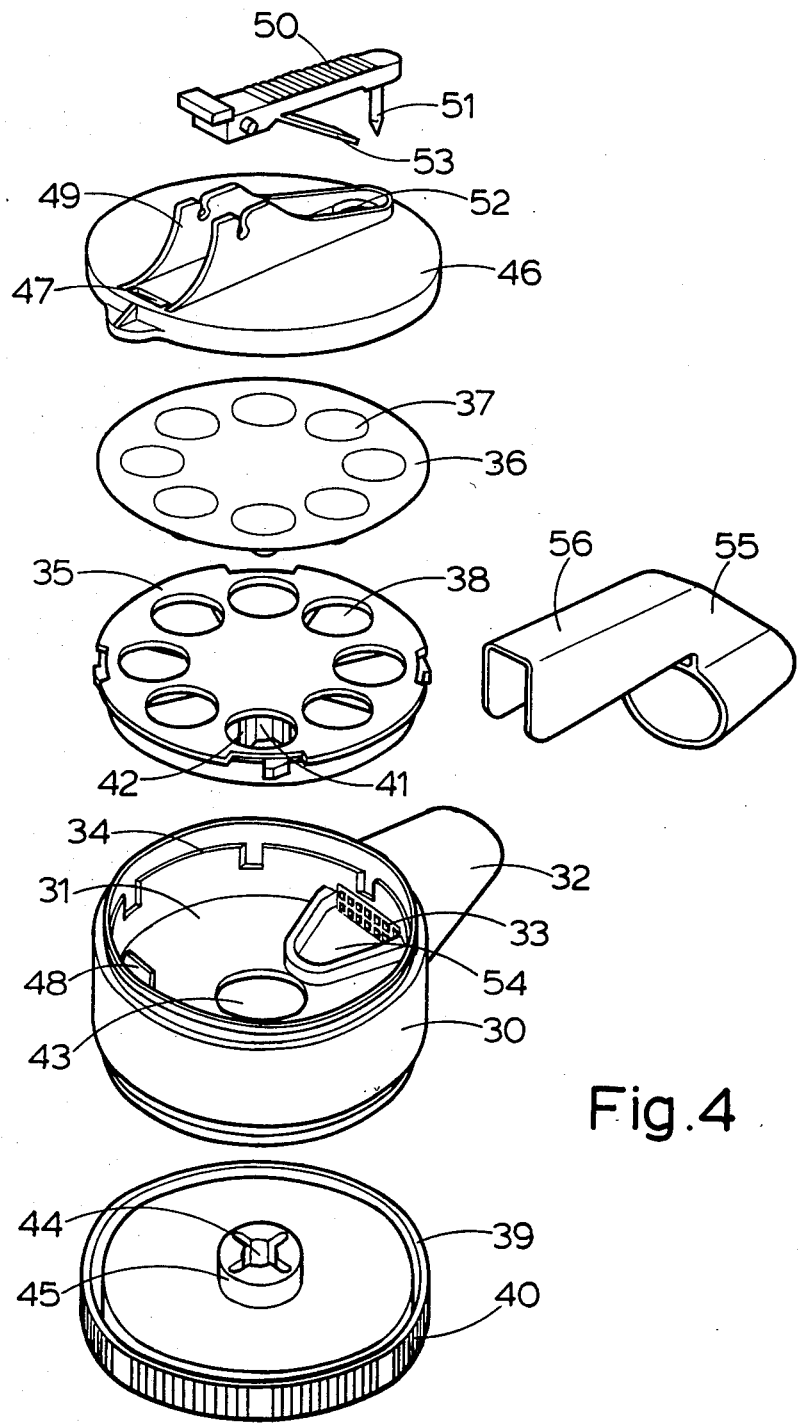
FIG. 4 is an exploded view of the embodiment illustrated in FIG. 3.

A modified device which does not use the clamp member 10 is illustrated in FIGS. 3 and 4. The device of this modification comprises a housing 30 having a chamber 31 therein. A mouthpiece 32 projects outwardly from the cylindrical wall of the housing 30 in a generally radial direction and communicates with the interior of the chamber 31. A perforated guard 33 is provided at the entrance to the mouthpiece 32. A rim or shoulder 34 runs round the inside wall of the chamber 31 to provide an annular support for a support member 35 in the form of a circular plate or disc. This support member is arranged to receive a blister pack 36. The blister pack 36 has a plurality of frangible containers 37 arranged in a circular row. These containers are in the form of "blisters" of a generally conical form as clearly shown in FIG. 4 and contain a medicament as described with reference to FIG. 1. The support member 35 has a plurality of holes 38 equal in number to the number of blisters 37 of the blister pack 36. The conical portion of one blister 37 is located in each of the holes 38 when the device is loaded and in use. An external rotatable member 39 with a knurled edge 40 is located in face contact with the bottom of the housing 30. A spindle or the like 41 with radial projections 42 extends centrally from the support member 35 through a hole 43 in the bottom of the housing 30 and into an opening 44 of complementary shape in a spigot 45 of the member 39. The spigot 45 passes through the hole 43 and the spindle 41 and 42 engages in the opening 44 so that rotation of the member 39 will cause similar rotation to the support member 35. A removable cover 46 fits on top of the housing 30. An opening 47 is provided in the cover 46 and engages a projection 48 in the housing 30 so as correctly to locate the cover. The cover 46 carries a bracket 49 on which a lever or trigger 50 is pivotally mounted. A plunger 51 is located on the lever or trigger 50 and extends through a hole 52 in the cover. A spring 53 is provided to bear between the trigger or lever 50 and the top of the cover 46 to urge the lever or trigger upwards.

The hole 52 is so positioned that each hole 38 in the support member 35 will register with this hole as the support member 35 is rotated.

When one of the holes 38 is in register with the hole 52 the trigger 50 can be depressed so that its plunger 51, which may be in the form of a needle, will pierce through the blister 37 located in that hole (i.e. pierce the top and the bottom of the blister) thereby to permit powder to exit from the blister. Some powder will fall into a tray-like compartment 54 inside the chamber 31. When the patient inhales, air passes through the pierced blister so that powder will be entrained in the airflow and will, with powder from the compartment 54, be withdrawn through the guard 33 and the mouthpiece 32. When the device is not in use, the mouthpiece 32 can be enclosed in a mouthpiece cover or sheath 55 which has a channel-like extension 56 which will engage with the bracket 49 to prevent the plunger 51 being depressed to enter through the hole 37.

When the device is in use and the patient inhales through the mouthpiece 32 it is, of course, essential for air to be able to enter the interior of the chamber 31. Any suitable air inlets can be provided. Conveniently, however, air can enter through the hole 52 the plunger or needle 51 being smaller in diameter than the diameter of the hole 52 so that it serves as an air inlet.

Figure 5:
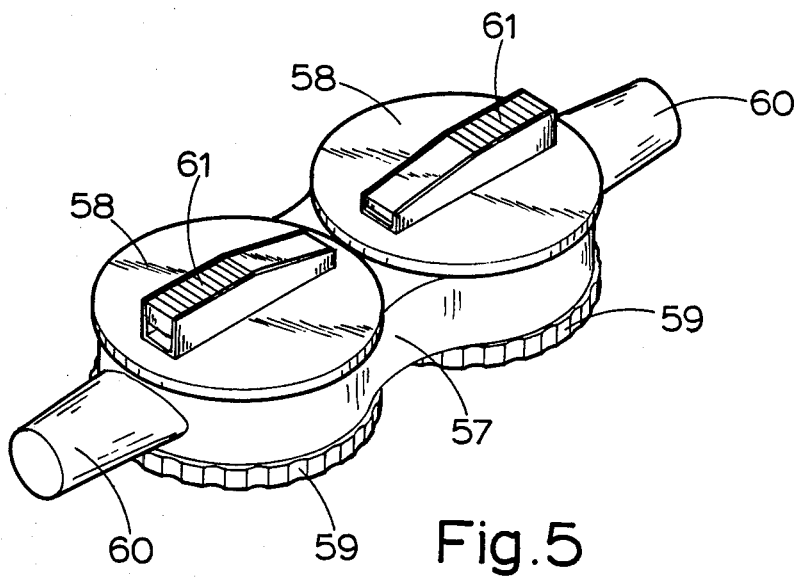
FIG. 5 is a perspective view of yet another embodiment of the invention.

FIG. 5 illustrates a modified device which can conveniently be used to administer two different medicaments to a patient at separate times. Treatment of certain patients does require that they inhale two different kinds of medicament. In the device illustrated in FIG. 5, a common housing 57 contains two chambers equivalent to the chamber 2 of the embodiment illustrated in FIG. 1 and 2 or to the chamber 31 of the embodiment illustrated in FIGS. 3 and 4. These two chambers are enclosed by removable covers 58 and blister packs contained in the chambers can be rotated in the manner previously described by rotation of knurled wheels, knobs or other members 59. Outlet mouthpieces 60 project outwardly from the common housing 57, each one of these outlets 60 leading into one of the chambers enclosed by the common housing. Trigger mechanisms 61 which function in the same manner as trigger mechanism 50 are provided to enable the blisters of the blister packs contained in the chambers to be pierced so that the contents thereof can be inhaled by the patient.

We claim:

1. A device for administering to patients medicaments contained in a plurality of containers arranged in a circle on a carrier, the said device being characterized by a housing with a chamber therein, an air inlet into the chamber, a circular disc having an axis substantially coaxial to the chamber axis and rotatable inside the chamber and provided with a plurality of apertures therethrough arranged in a circle, said apertures being sized and positioned so that each aperture is adapted to be aligned with a different container, the said disc being arranged so that the carrier can be placed in contact with one face of the disc with one of the containers located in each one of the apertures, an outlet through which a patient may inhale leading out of the chamber, an opening in said housing alignable with respective ones of the apertures in the disc as the disc is rotated, a plunger operatively connected to said housing and having a penetrating member, said penetrating member being displaceable to pass through said opening and the corresponding aperture in the disc registered with it thereby to penetrate and open a container located in the aperture so that the medicament will be released from the container and entrained in the air flow produced by a patient inhaling through the outlet, and means between said disc and said housing for rotatably indexing the disc to register each of the apertures in turn with the housing opening.

2. A device as claimed in claim 1, wherein the outlet is a mouthpiece which leads out of the chamber in a substantially radial direction.

3. A device as claimed in claim 1, wherein a perforated guard is positioned so that air and medicament inhaled through the outlet will first pass through the guard.

4. A device as claimed in claim 1, wherein a rotatable member is located outside the chamber and is connected with the circular disc so that rotation of the said member will cause rotation of the circular disc.

5. A device as claimed in claim 1, wherein a rim is defined inside the chamber and the circular disc is fitted inside the chamber and on the support but is removable to permit a carrier to be placed on the rim and thereafter clamped between the circular disc and the rim.

6. A device as claimed in claim 1 wherein the chamber has a cover which is removable to permit a carrier to be inserted in the chamber and placed on the support, the plunger being carried by the cover.

7. A device as claimed in claim 1, wherein a removable cover encloses said outlet, said cover having means for preventing operation of the plunger when the cover is fitted on said outlet.

8. A device as claimed in claim 1 wherein said carrier is a circular disc having a plurality of frangible containers containing a medicament in particulate form.

9. A device for the administration of medicaments to a patient comprising a common housing in which are located a plurality of devices as claimed in claim 1.

10. A device as claimed in claim 1, wherein the carrier and containers are provided by a blister pack.

* * * * *